US009433947B2

(12) United States Patent
Wo et al.

(10) Patent No.: US 9,433,947 B2
(45) Date of Patent: Sep. 6, 2016

(54) CENTRIFUGAL MICROFLUIDIC DISK AND PROCESSING METHOD USING THE SAME

(71) Applicant: National Taiwan University, Taipei (TW)

(72) Inventors: Andrew Man Chung Wo, Taipei (TW); Chen-Lin Chen, Taipei (TW); Cheng-Wei Yang, Taipei (TW); Wei-Hao Lian, Taipei (TW)

(73) Assignee: National Taiwan University, Taipei (TW)

( * ) Notice: Subject to any disclaimer, the term of this patent is extended or adjusted under 35 U.S.C. 154(b) by 559 days.

(21) Appl. No.: 13/762,397

(22) Filed: Feb. 8, 2013

(65) Prior Publication Data

US 2013/0210599 A1     Aug. 15, 2013

Related U.S. Application Data

(60) Provisional application No. 61/633,565, filed on Feb. 14, 2012, provisional application No. 61/633,566, filed on Feb. 14, 2012.

(51) Int. Cl.
| | |
|---|---|
| *B01L 3/00* | (2006.01) |
| *B04B 7/08* | (2006.01) |
| *B81B 1/00* | (2006.01) |
| *G01N 21/07* | (2006.01) |

(52) U.S. Cl.
CPC ............ *B04B 7/08* (2013.01); *B01L 3/502753* (2013.01); *B81B 1/00* (2013.01); *G01N 21/07* (2013.01); *B01L 2200/0652* (2013.01); *B01L 2200/0668* (2013.01); *B01L 2300/0806* (2013.01); *B01L 2400/0409* (2013.01); *B01L 2400/0487* (2013.01)

(58) Field of Classification Search
CPC ................. B01L 3/502753; B01L 2200/0668; B01L 2200/0652; B01L 2300/0806; B01L 2400/0487; B01L 2400/0409; B04B 7/08
See application file for complete search history.

(56) References Cited

U.S. PATENT DOCUMENTS

| | | | |
|---|---|---|---|
| 2006/0021952 A1 | 2/2006 | Skinkle et al. | |
| 2008/0108120 A1* | 5/2008 | Cho ................. | B01L 3/502753 422/72 |
| 2010/0197476 A1 | 8/2010 | Rosiello | |

FOREIGN PATENT DOCUMENTS

| | | |
|---|---|---|
| DE | 19634413 | 3/1998 |
| TW | I312697 | 8/2009 |
| TW | 201107038 | 3/2011 |

OTHER PUBLICATIONS

"Office Action of Taiwan Counterpart Application", issued on Jun. 23, 2015, p. 1-p. 4, in which the listed references were cited.

* cited by examiner

*Primary Examiner* — Timothy Cleveland
(74) *Attorney, Agent, or Firm* — Jianq Chyun IP Office

(57) ABSTRACT

This invention provides a centrifugal microfluidic disk and methods for separating targets or cells and collecting the targets or cells in the centrifugal microfluidic disk by using the density gradient.

19 Claims, 7 Drawing Sheets

CENTRIFUGAL MICROFLUIDIC DISK AND PROCESSING METHOD USING THE SAME

CROSS-REFERENCE TO RELATED APPLICATION

This application claims the priority benefits of U.S. provisional applications Ser. No. 61/633,565, filed on Feb. 14, 2012, and Ser. No. 61/633,566, filed on Feb. 14, 2012. The entirety of each of the above-mentioned patent applications is hereby incorporated by reference herein and made a part of this specification.

BACKGROUND OF THE INVENTION

1. Field of the Invention

The present invention generally relates to a separation method. More particularly, the present invention relates to a centrifugal microfluidic disk and a processing method using the same.

2. Description of Related Art

Among the microfluidic technology widely applied in biological, medical and biochemical fields, chip-based microfluidic devices and centrifugal-based microfluidic devices are two major categories. For the centrifugal-based microfluidic devices, the centrifugal force as a result of spinning is utilized to isolate or purify biological samples.

During the operation of the centrifugal device, the first set of sample (e.g. cells, blood, or biological fluids, etc.) is injected and stored on-disk prior to spinning and the next set of sample has to be hold during spinning. Due to the design of non-continuous fluidic input of the samples, the centrifugal microfluidic devices are incongruous for the handling of samples of large volumes. Hence, the centrifugal microfluidic platform has limited commercial success and generally used as a research tool.

SUMMARY OF THE INVENTION

This invention provides a centrifugal microfluidic disk and methods for separating and collecting cells in the centrifugal microfluidic disk by using the density gradient. As the centrifugal microfluidic disk is applicable for an automated workstation of continuous fluidic input, samples of large volumes can be easily processed.

The present invention is directed to a centrifugal microfluidic disk having at least a sample inlet for loading a fluidic sample, a separation chamber, a settling chamber, a collection chamber and a waste outlet connected to the collection chamber. One end of the separation chamber is connected to the sample inlet, while the other end of the separation chamber is connected to a junction. The settling chamber is arranged surrounding the separation chamber but is separate from the separation chamber. The settling chamber is connected with the separation chamber through a plurality of flow channels located in-between, so that the fluidic sample flows between the separation chamber and the settling chamber. The collection chamber is connected to the junction through a conveying channel, and the junction extends vertically and communicates with the conveying channel and the separation chamber.

The present invention provides a method for separating a target from a fluidic sample by using a microfluidic disk. The method includes at least the process step of introducing the fluidic sample into the microfluidic disk, of spinning the microfluidic disk to drive the fluidic sample flowing radially outward into the separation chamber and of drawing the target out from the collection chamber.

In order to make the above and other features and advantages of the present invention more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

Common reference numerals are used throughout the drawings and the detailed description to indicate the same elements. The present invention will be more apparent from the following detailed description taken in conjunction with the accompanying drawings.

DESCRIPTION OF THE EMBODIMENTS

The present invention is directed to a centrifugal microfluidic disk and methods for processing (i.e. separating, collecting and/or labeling) cells or target molecules in the centrifugal microfluidic disk by using the density gradient. Also, the present invention provides an automated workstation for operating the centrifugal microfluidic disk and performing the processing of the biological sample.

The centrifugal microfluidic disk or the separation method as disclosed in the present invention may be applied to process various types of samples, including the whole blood sample, the plasma fluids, urine or other body or biological fluids.

In the tumor metastatic process, invasive tumor cells in the primary site tend to shed cells into the blood stream, transfer to other organs and grow into new tumors. However, it is very difficult to spot these metastasized cells in the blood stream as these metastasized cells are very scarce when compared to the hematologic cells (about 1 tumor cell per 1 billion cells). It has been noticed that these metastasized cells circulating in the blood stream, i.e. circulating tumor cells (CTCs), may be useful in providing potentially predictive information regarding tumor metastasis and/or efficacy of a particular therapy. For the experimentation purposes, these rare cells, such as CTCs, may be separated and collected from the blood sample.

In the following embodiment, the whole blood is used as an example of the biological sample and the separation and collection of the rare cells from the whole blood may be used for describing the operation of the microfluidic disk and the related automation station.

Figure 1A:
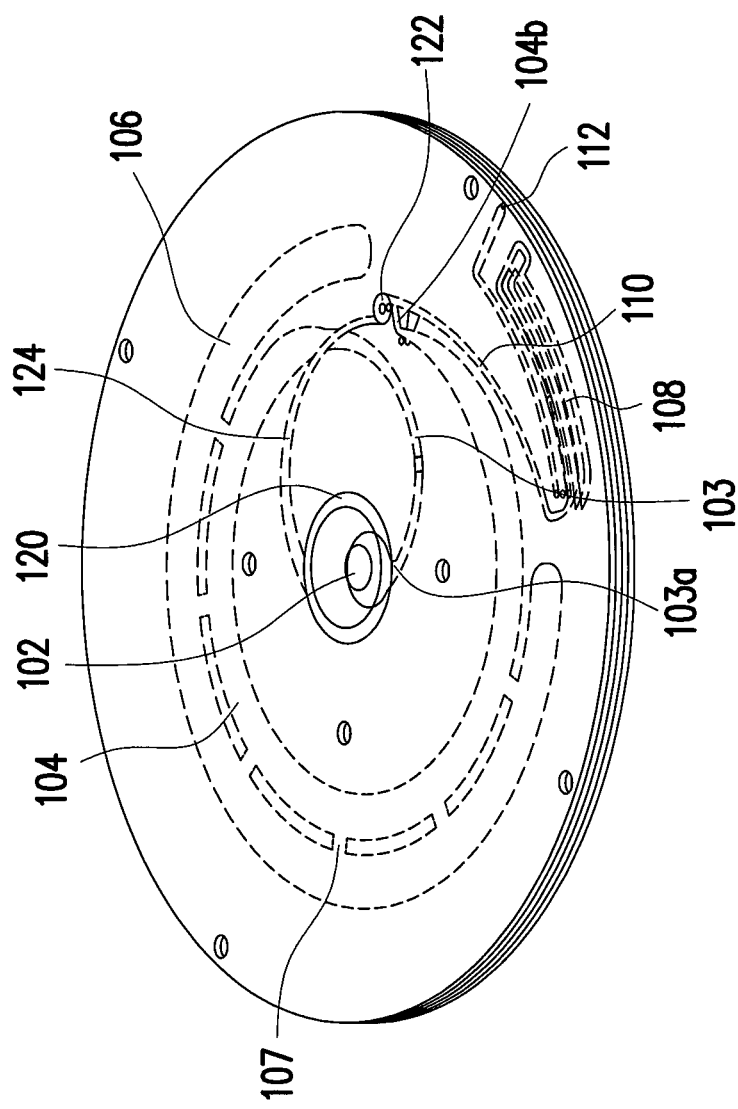
FIG. 1A schematically illustrates a three-dimensional view of a centrifugal microfluidic disk according to an embodiment of this invention.
Figure 1C:
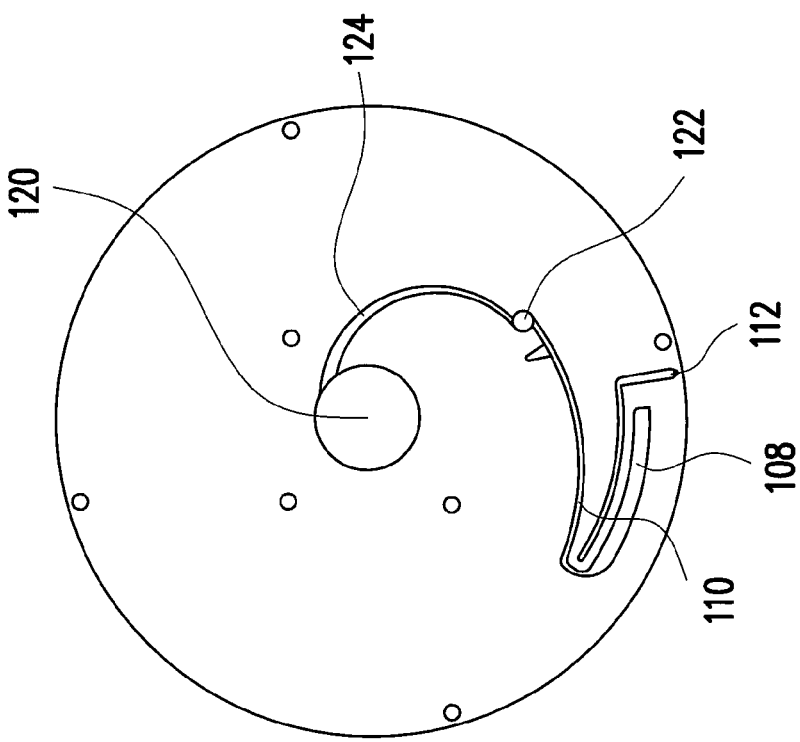
FIG. 1C schematically illustrates another cross-sectional view of the centrifugal microfluidic disk of FIG. 1A.
Figure 1B:
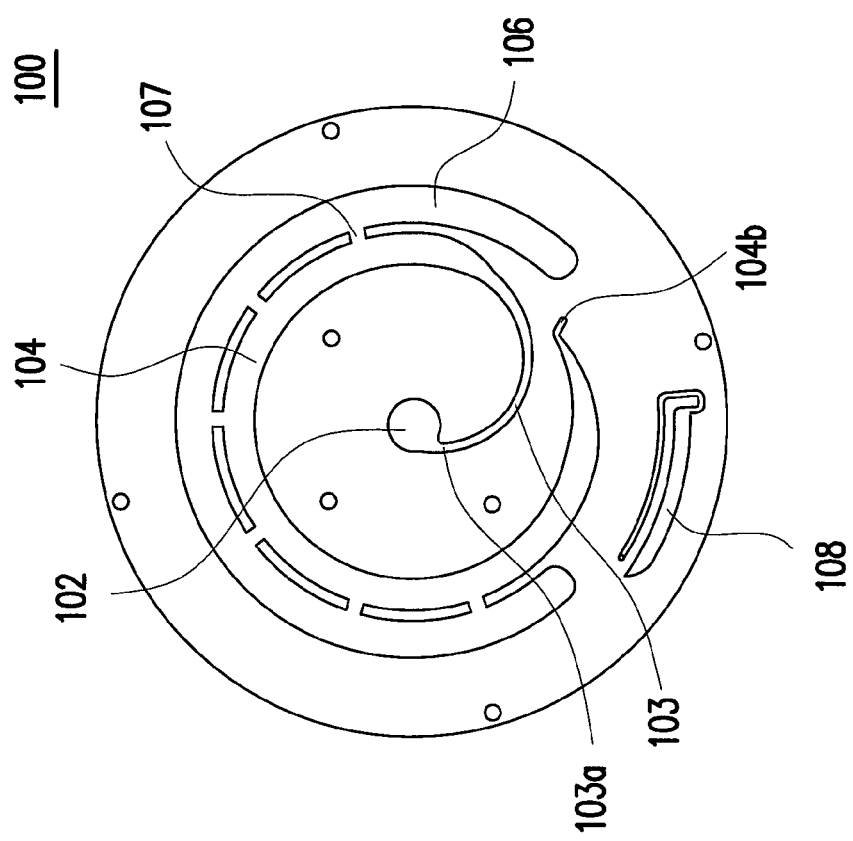
FIG. 1B schematically illustrate one cross-sectional view of the centrifugal microfluidic disk of FIG. 1A.

FIG. 1A schematically illustrates a three-dimensional view of a centrifugal microfluidic disk according to an embodiment of this invention. FIG. 1B schematically illustrates a cross-sectional view of the centrifugal microfluidic disk of FIG. 1A, while FIG. 1C schematically illustrates another cross-sectional view of the centrifugal microfluidic disk of FIG. 1A. FIG. 1B shows a cross-section of a deeper portion (lower level) of the disk of FIG. 1A, while FIG. 1C shows a cross-section of a shallower portion (upper level) of the disk of FIG. 1A. The cross-sections of FIGS. 1B and 1C are taken transversely to the thickness direction of the disk of FIG. 1A. The centrifugal microfluidic disk 100 may be a round or elliptical disk and the microfluidic disk 100 may be fabricated as several slices and then assembled or stacked together. The material of the microfluidic disk 100 may be a plastic material, such as polymethyl methacrylate (PMMA), or other thermoplastics. The diameter of the microfluidic disk 100 may ranges from 6 to 18 centimeters, preferably 12 centimeters, for example.

Referring to FIGS. 1A-1C, the centrifugal microfluidic disk 100 at least includes a sample inlet 102, a separation chamber 104, a settling chamber 106, a collection chamber 108 and a waste outlet 112. The sample inlet 102 is located on a central position of the disk 100 and the sample may be loaded into the disk 100 through the sample inlet 102. The separation chamber 104 is connected with the sample inlet 102 through a connecting channel 103. The connecting channel 103 and the separation chamber 104 are jointly designed to be a spiral shape spiraling outward from the central sample inlet 102. The separation chamber 104 has an arc shape and the arc-shape portion (the portion substantially along the circumferential edge of the disk) of the separation chamber 104 has a dimension of about 3 centimeters. The connecting channel 103 (the portion connected to the sample inlet to the circumferential portion) has a dimension of about 0.5 centimeters.

The settling chamber 106 is arranged surrounding the separation chamber 104 but is separate from the separation chamber 104 with a distance in-between. The settling chamber 106 is connected with the separation chamber 104 through a plurality of flow channels 107 located in-between, so that the injected fluid can flow between the separation chamber 104 and the settling chamber 106. One end 103a of the connecting channel is physically connected to the sample inlet 102, while one end 104b of the separation chamber 104 is physically connected to a junction 122.

As shown in FIG. 1C, the disk 100 includes a chemical inlet or reagent inlet 120 at the central position of the disk 100 and reaction reagents may be loaded into the disk 100 via the reagent inlet 120. The reagent inlet 120 and the sample inlet 102 are both round openings, but the reagent inlet 120 and the sample inlet 102 are of different sizes, are located at different levels and arranged in a concentric way. The reagent inlet 120 located at the upper level has a size larger than the size of the sample inlet 102 located at the lower level. The reagent inlet 120 is connected to the junction 122 through a linking channel 124. The junction 122 is further connected to the collection chamber 108 through a conveying channel 110. The junction 122 extends vertically and communicates with the conveying channel 110 located at the upper level and the separation chamber 104 located at the lower level. The waste outlet 112 is connected to the collection chamber 108, so that the needless fluid or running solution is discharged from the waste outlet 112. Also, the separated or collected sample stored in the collection chamber 108 may be removed from the disk.

Figure 2:
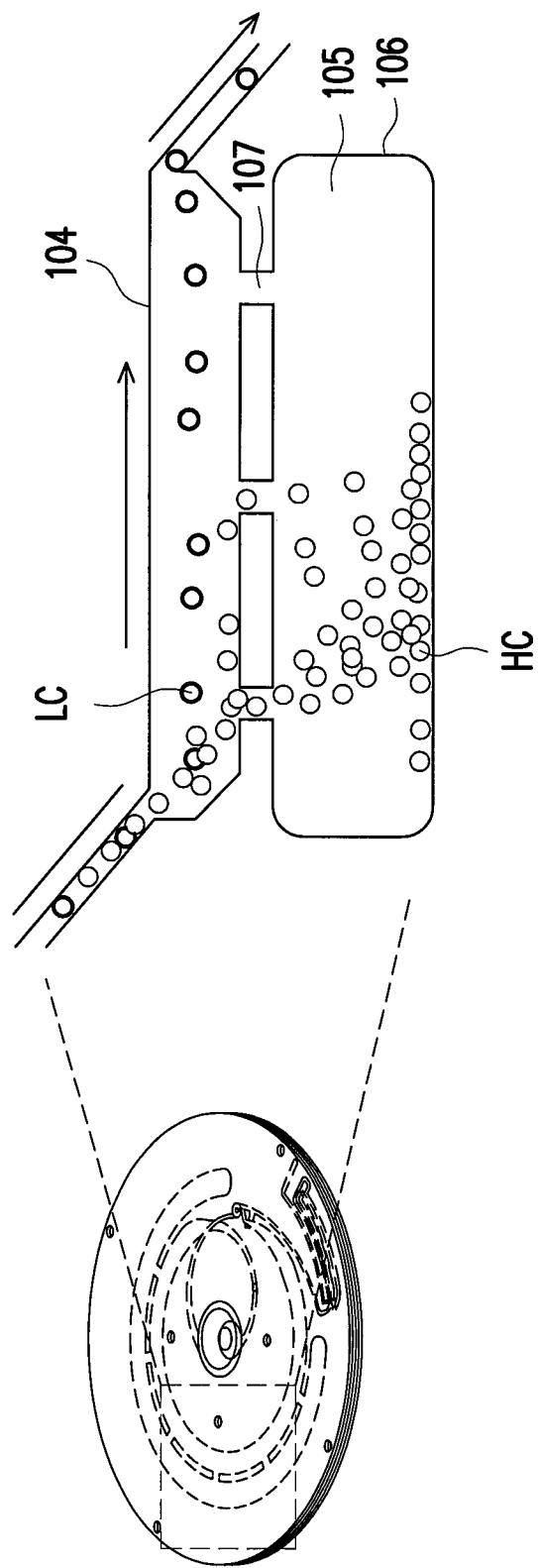
FIG. 2 schematically illustrates a cross-sectional view along the thickness direction of a portion of a centrifugal microfluidic disk according to one embodiment of the present invention.

FIG. 2 schematically illustrates a cross-sectional view along the thickness direction of a portion of a centrifugal microfluidic disk according to one embodiment of the present invention. FIG. 2 focuses on the portion of the separation chamber and the settling chamber in order to show the principle of cell or molecule separation. The density gradient solution 105 is firstly loaded into the separation chamber 104 and the settling chamber 106 prior to the loading of the sample. The density gradient solution 105 may be a Ficoll-Paque solution (Ficoll-paque™ plus, GE Healthcare, No. 17-1440-02), for example. During spinning of the disk 100, the centrifugal force drives the fluid (the fluidic sample+the buffer) flowing radially outward from the central sample inlet 102 outward along the spiral-shaped connecting channel 103 and the separation chamber 104 and then outward toward the settling chamber 106 that is arranged closer to the circumferential edge of the disk 100 and surrounding the separation chamber 104. That is, the fluidic sample, such as the blood sample containing light cells LC and heavy cells HC, loaded from the sample inlet flows into the separation chamber 104 (flow direction indicated by the arrow). Through the act of the centrifugal force and the selection of the density gradient solution 105, the light cells LC or light molecules are suspended and flows from the separation chamber 104 further into the collection chamber (flow direction indicated by the arrow), while the heavy cells HC or heavy molecules are settled and washed into the settling chamber 106. The flow path of the sample starts from the sample inlet 102, along the connecting channel 103, the separation chamber 104 and the settling chamber 106 and a portion of the sample ends at the collection chamber 108.

By adjusting the flow conditions and/or the density of the density gradient solution 105, the target cells or molecules can be easily isolated from the biological sample and stayed in the collection chamber 108.

As the target cells or molecules are collected in the collection chamber 108, further treatment(s) may be performed to process the target cells or molecules. For example, the target cells may be further labeled within the collection chamber 108 before the withdrawal of the target cells. In this case, instead of the sample inlet 102, the labeling reagent may be loaded from the reagent inlet 120, pass through the linking channel 124, the junction 122, the conveying channel 110 and flow into the collection chamber 108 (FIG. 1A). The flow path of the chemical or the labeling reagent starts from the chemical or reagent inlet 120, through the linking channel 124, the junction 122, the conveying channel 110 and ends at the collection chamber 108, without entering the separation chamber or the settling chamber.

Figure 3:
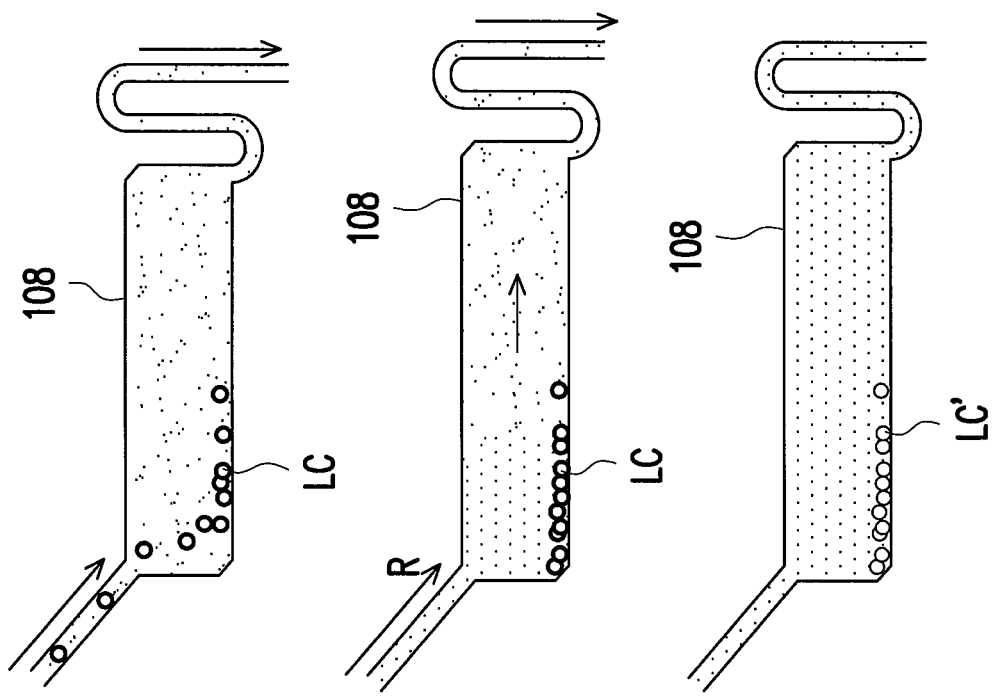
FIG. 3 schematically illustrates a cross-sectional view along the thickness direction of a portion of a centrifugal microfluidic disk according to one embodiment of the present invention.
Figure 3:
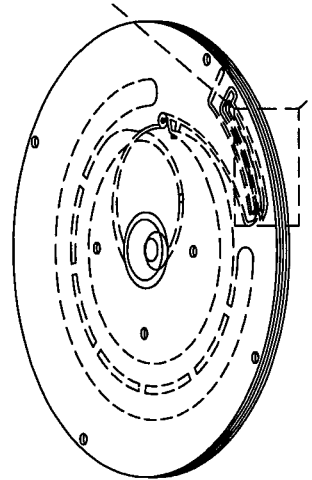

FIG. 3 schematically illustrates a cross-sectional view along the thickness direction of a portion of a centrifugal microfluidic disk according to one embodiment of the present invention. FIG. 3 focuses on the portion of the collection chamber in order to show the principle of cell labeling. As shown in the top part of FIG. 3, light cells LCs are collected in the collection chamber 108 (flow direction indicated by the arrow). Later on, the reagent R (such as a chemical, a fluorescent dye, antibodies, immuno-markers, quantum dots, magnetic beads, or other labeling or sample preparation materials) is loaded into the collection chamber 108 and incubated with the light cells LC (shown in the middle part of FIG. 3) and then the labeled light cells LC' are obtained after incubation (shown in the bottom part of FIG. 3). Finally, the washing buffer is injected to wash out the unreacted labeling reagent. The labeling process may be any available labeling process, such as immuno-labeling, fluorescence labeling or magnetic bead labeling.

In this embodiment, the labeling process is simply performed once, but if necessary, several times of labeling (i.e. multiple labeling or multi-marker labeling) may be performed to the target(s) collected in the collection chamber.

The centrifugal microfluidic disk(s) according to embodiments of the present invention can operate together with an automated workstation.

Figure 4:
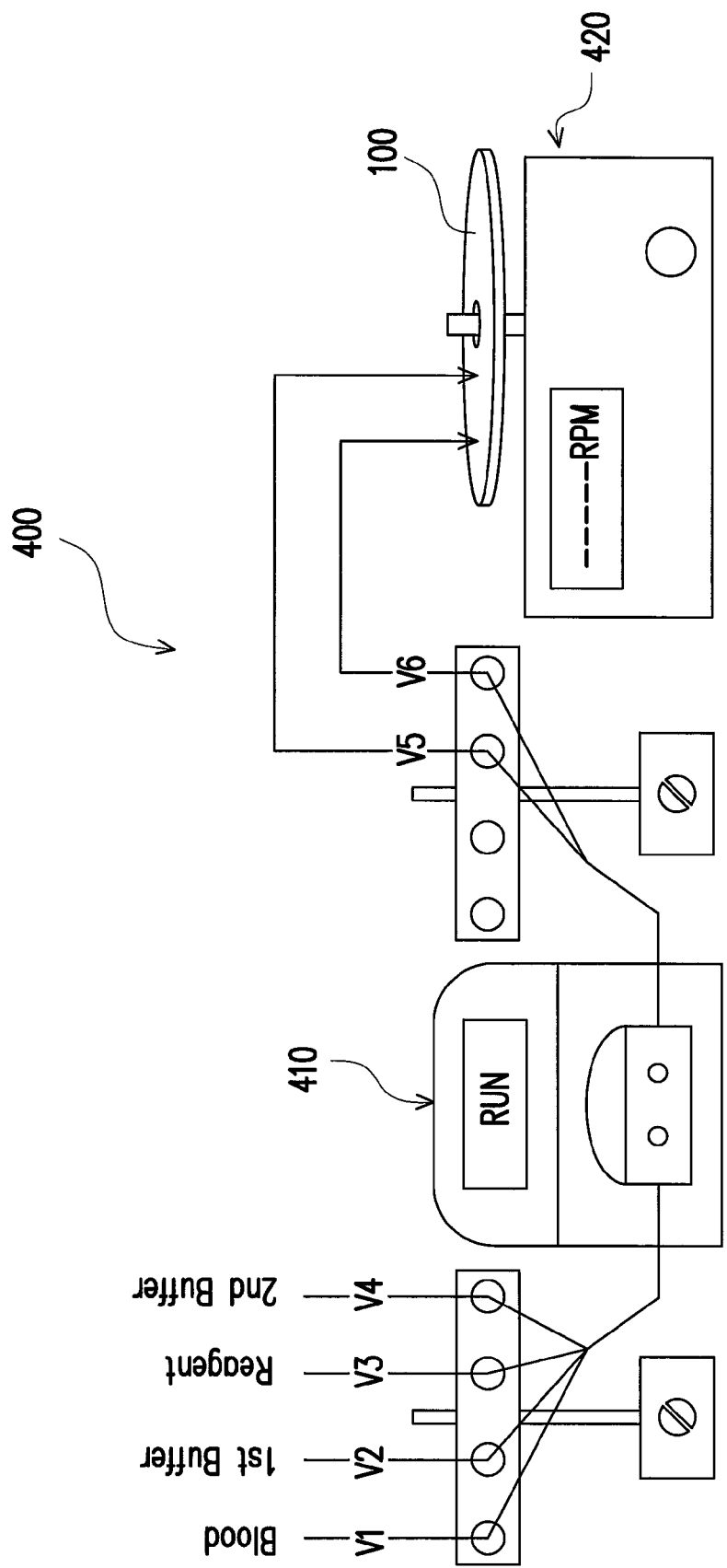
FIG. 4 schematically illustrates an automated workstation according to an embodiment of the present invention.

FIG. 4 schematically illustrates an automated workstation according to an embodiment of the present invention. The automated workstation 400 includes at least a peristaltic pump 410, a rotation platform 420 and pinch valves V1-V6. The external peristaltic pump 410 can drives the fluid or the buffer solution to provide a stable flow rate for the blood sample. The pinch valves V1-V6 allow fast fluid handling and shut-off so that the entire workstation can be easily programmable. The rotation platform 420 may be powered by a motor so as to spin the microfluidic disk at a high speed for high throughput handing. The automated workstation 400 adopts continuous fluidic input, continually pumping the fluidic sample (such as the blood sample) and the buffer by the peristaltic pump and injecting the blood sample continuously during the disk operation. The flow mechanism of the automated workstation 400 is shown in FIG. 4 and the flow direction is marked by the arrow. For example, the pinch valves V1-V4 control the loading (input) of the blood sample, the first buffer, the reagent solution and the second buffer respectively. Driving by the peristaltic pump 410, the blood sample is controlled by the pinch valve V5 and injected into the inner sample inlet. Also, driving by the peristaltic pump 410, the reagent solution is controlled by the pinch valve V6 and injected into the outer reagent inlet. The first buffer may be a running buffer, while the second buffer may be a washing buffer. The reagent solution may include one or more types of fluorescent dyes, antibodies, immuno-markers, or even labeled magnetic beads.

The processing steps of the fluidic sample (such as the blood sample containing light cells and heavy cells) in the automated workstation may be summarized as: introducing the blood sample into the microfluidic disk within the automated workstation; spinning the microfluidic disk by the rotation platform to drive the blood sample flowing radially outward into the separation chamber, wherein the light cells of the blood sample flow into the collection chamber, while the heavy cells are deposited in the settling chamber; and collecting the light cells from the collection chamber. The operation details may be exemplified as the following steps:

a) fill the blood sample, Ficoll-Paque™ plus solution, the buffers and the reagent solution into the storage tubes.

b) spin the microfluidic disk at 2000~4000 rpm (revolution per minute).

c) during spinning, load and pump Ficoll-Paque™ plus solution from the sample inlet into the disk with a flow rate 50~5000 microliters/minute.

d) pump PBS/buffer into the disk with a flow rate 50~5000 microliters/minute.

e) load and pump the blood sample and the buffer into the disk with a flow rate 50~2000 microliters/minute.

f) pump PBS/buffer into the disk with a flow rate 50~5000 microliters/minute.

g) from the reagent inlet, load and pump the reagent solution into the disk with a flow rate 50~1000 microliters/minute.

h) spin the microfluidic disk at 0~500 rpm for 10~60 minutes used for incubation.

i) spin the microfluidic disk at 2000~4000 rpm.

j) pump PBS/buffer into the disk with a flow rate 50~5000 microliters/minute.

k) stop spinning and draw out the collected cells in the collection chamber.

To characterize the performance of the disk platform, several cancer cell lines were used to represent the target cells. These cell lines are breast cancer cell lines MCF7 and MDA-MB-231, prostate cancer cell line PC3, and colorectal cancer cell line Colo205. The blood samples were collected from healthy human volunteers and about 100 cancer cells were mixed into 1 ml of the whole blood to simulate the real cases with rare cells.

Figure 5A:
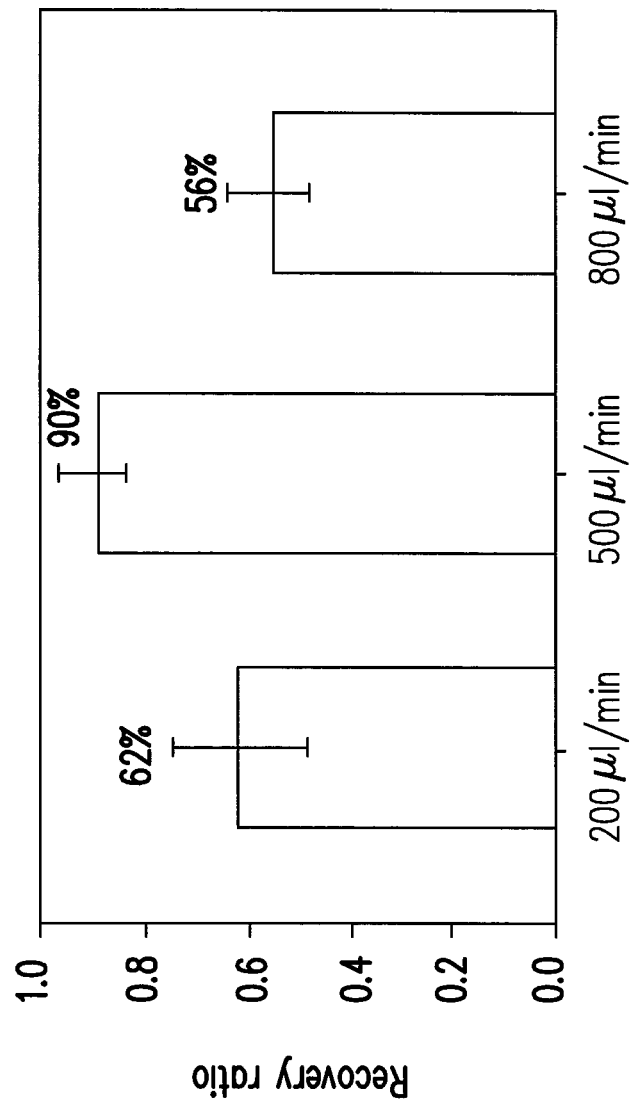
FIG. 5A shows the relationship between flow rate and the recovery ratio of cell line MCF7.
Figure 5B:
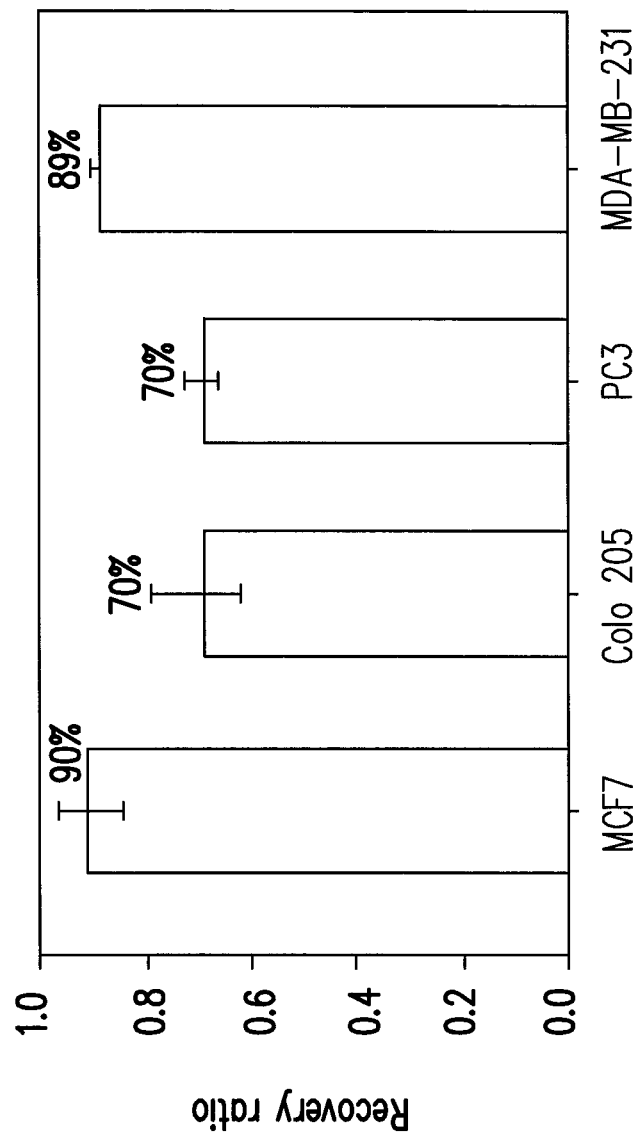
FIG. 5B shows the recovery ratios of different types of cell lines.

For determining the optimal flow rate of this disk platform, we prepared the sample for the experiments by using spiked MCF7 that was labeled with anti-EpCAM-PE and mixing with 1 ml of blood. FIG. 5A shows the relationship between flow rate and the recovery ratio of cell line MCF7. The result indicated that the optimal flow rate in the present experiment is 500 microliters/minute and the recovery ratio (i.e. the harvest amount) is around 0.9 (90% in percentage). Using the flow rate of 500 microliters/min for further experiments, different types of cancer cell lines were tested. FIG. 5B shows the recovery ratios of different types of cell lines. The recovery ratios of different types of cancer cell lines using the disk platform range from 60%~90%, generally above 70%. These results demonstrated that the microfluidic disk and the workstation can efficiently separate and collect very small amount of cells (i.e. rare cells) from the whole blood.

In the centrifugal system disclosed in this invention, continuous-flow microfluidic operation can provide significant advantages, including large sample volumes (up to 20 ml), simple implementation and less pollution. As described previously, the relative locations of the sample inlet and the reagent inlet can be arranged in a concentric way or in an eccentric way, and the centrifugal disk may be spun with a rotating shaft located at the center part of the disk or without a main shaft of rotation.

This advanced centrifugal microfluidic disk have many potential applications in biological, biochemical and medicinal fields. The microfluidic disk is compatible with fully automated sample preparation and is able to hold flexible sample volumes (ranging from 0.5 ml to 20 ml). The microfluidic disk can achieve high recovery rates up to 60%~90%. Further, the automated workstation using the microfluidic disk in fact integrates continuous density gradient separation and multi-marker labeling.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily being drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention.

What is claimed is:

1. A centrifugal microfluidic disk, at least comprising:
   a sample inlet, located at a first level for loading a blood or biological sample;
   a separation chamber, connected to the sample inlet, wherein the separation chamber contains an arc-shape portion and a density gradient solution is loaded into the separation chamber;
   a chemical inlet, located at a second level for loading a chemical;
   a collection chamber, connected to the separation chamber;
   a conveying channel, connected to the collection chamber; and
   a junction extending vertically from the first level to the second level and connecting the conveying channel located at the second level and the separation chamber located at the first level, wherein the chemical inlet and the sample inlet are located at different levels.

2. The centrifugal microfluidic disk of claim 1, wherein a flow path of the chemical inlet is located differently to a flow path of the sample inlet.

3. The centrifugal microfluidic disk of claim 1, wherein the arc-shape portion of the separation chamber is arranged surrounding a disk center.

4. The centrifugal microfluidic disk of claim 1, further comprising at least a settling chamber, wherein the settling chamber is arranged radially outward from the separation chamber, and the separation chamber and the settling chamber are connected through at least one flow channel therebetween.

5. The centrifugal microfluidic disk of claim 1, wherein the collection chamber is located radially outward from the separation chamber and closer to a circumferential edge of the centrifugal microfluidic disk.

6. The centrifugal microfluidic disk of claim 2, further comprising a linking channel connected between the chemical inlet and the collection chamber and at least one waste outlet connected to the collection chamber.

7. A centrifugal microfluidic disk, at least comprising:
   a sample inlet, located at a first level for loading a blood or biological sample;
   a separation chamber, connected to the sample inlet, wherein the separation chamber contains an arc-shape portion and a density gradient solution is loaded into the separation chamber; and
   a settling chamber, connected to the separation chamber;
   a chemical inlet, located at a second level for loading a chemical;
   a collection chamber, connected to the separation chamber;
   a conveying channel, connected to the collection chamber; and
   a junction extending vertically from the first level to the second level and connecting the conveying channel located at the second level and the separation chamber located at the first level, wherein the chemical inlet is connected to the collection chamber via a linking channel and a first flow path of the sample is different than a second flow path of the chemical, and the chemical inlet and the sample inlet are located at different levels.

8. The centrifugal microfluidic disk of claim 7, wherein the first flow path of the sample starts from the sample inlet, along the separation chamber and connected to the collection chamber.

9. The centrifugal microfluidic disk of claim 7, the second flow path of the chemical starts from the chemical inlet, through the linking channel and connected to the collection chamber.

10. The centrifugal microfluidic disk of claim 7, wherein the arc-shape portion of the separation chamber is arranged surrounding a disk center.

11. The centrifugal microfluidic disk of claim 7, wherein the settling chamber is arranged surrounding the separation chamber, and the separation chamber and the settling chamber are connected through at least one flow channel therebetween.

12. The centrifugal microfluidic disk of claim 7, wherein the collection chamber is located outward from the separation chamber and closer to a circumferential edge of the centrifugal microfluidic disk.

13. A method for separating a target from a sample, comprising:
   providing a microfluidic disk, wherein the microfluidic disk at least comprises:
      a sample inlet located at a first level for loading a blood or biological sample;
      a separation chamber, connected to the sample inlet, wherein the separation chamber contains an arc-shape portion;
      a chemical inlet, located at a second level;
      a collection chamber, connected to the separation chamber through at least a flow channel located in-between;
      a conveying channel, connected to the collection chamber; and
      a junction extending vertically from the first level to a second level and connecting the conveying channel located at the second level and the separation chamber located at the first level, wherein the first and second levels are different levels;
   introducing the sample into the sample inlet of the microfluidic disk and loading a density solution into the separation chamber; and
   spinning the microfluidic disk to drive the sample flowing outward through the separation chamber, wherein the target is separated from the sample by the density solution in the separation chamber and further flows through the junction and the conveying channel into the collection chamber.

14. The method of claim 13, further comprising a settling chamber for receiving a non-target portion of the sample.

15. The method of claim 13, further comprising filling a portion of the microfluidic disk with the density gradient solution before introducing the sample.

16. The method of claim 13, during spinning of the microfluidic disk, a centrifugal force drives a non-target portion of the sample flowing into the settling chamber and prevents the target of the sample from entering into the settling chamber.

17. The method of claim 16, further comprising drawing out the target from the collection chamber through an outlet connected to the collection chamber of the microfluidic disk.

18. The method of claim 17, further comprising injecting a chemical solution into the collection chamber so as to perform labeling or sample preparation in the collection chamber before drawing out the target from the collection chamber.

19. The method of claim 18, wherein the chemical solution comprises one or more types of chemicals, fluorescent dyes, antibodies, immuno-markers, quantum dots, magnetic beads, labeling materials or sample preparation materials.

* * * * *